United States Patent
Ducharme et al.

(10) Patent No.: US 10,456,195 B2
(45) Date of Patent: Oct. 29, 2019

(54) ABLATION OVERTUBE

(75) Inventors: Richard W. Ducharme, Winston-Salem, NC (US); Tyler E. McLawhorn, Winston-Salem, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 441 days.

(21) Appl. No.: 13/209,763

(22) Filed: Aug. 15, 2011

(65) Prior Publication Data
US 2012/0053403 A1 Mar. 1, 2012

Related U.S. Application Data

(60) Provisional application No. 61/378,732, filed on Aug. 31, 2010.

(51) Int. Cl.
*A61B 18/14* (2006.01)
*A61B 1/00* (2006.01)
(Continued)

(52) U.S. Cl.
CPC ...... *A61B 18/1492* (2013.01); *A61B 1/00135* (2013.01); *A61B 1/012* (2013.01); *A61B 1/2736* (2013.01); *A61B 18/1206* (2013.01); *A61B 2018/00196* (2013.01); *A61B 2018/00291* (2013.01); *A61B 2018/00577* (2013.01); *A61B 2018/126* (2013.01); *A61B 2018/1437* (2013.01); *A61B 2018/1472* (2013.01);
(Continued)

(58) Field of Classification Search
CPC .... A61M 2025/0233; A61M 2025/028; A61M 25/02; A61N 1/0509; A61N 1/0517;
A61N 1/36007; A61N 1/372; G01N 27/126; A61B 1/0011; A61B 1/041; A61B 1/0638; A61B 18/1487; A61B 1/00071; A61B 1/00135; A61B 1/00137
USPC .............. 600/101, 184; 606/1, 907, 914–916
See application file for complete search history.

(56) References Cited

U.S. PATENT DOCUMENTS 4,664,120 A * 5/1987 Hess ...................... A61N 1/056
600/374
5,035,695 A * 7/1991 Weber, Jr. .......... A61B 18/1402
604/35

(Continued)

OTHER PUBLICATIONS

International Search Report dated Nov. 17, 2011 for International Application No. PCT/US2011/047708.

(Continued)

*Primary Examiner* — Alexandra L Newton
(74) *Attorney, Agent, or Firm* — Brinks Gilson & Lione

(57) ABSTRACT

An energy delivery system and a method of delivering energy to a tissue are provided. The energy delivery system includes an overtube. The overtube includes a body having a proximal portion, a distal portion and a lumen extending at least partially therethrough. The proximal portion is adapted to be positioned over a distal portion of an endoscope. The body also includes a first plurality of openings formed in the body and connected to the lumen and an electrode operably connected to the body and extending over at least a portion of a surface of the body. The lumen is operably connectable to a vacuum source and the electrode is operably connectable to a power source.

17 Claims, 9 Drawing Sheets

(51) Int. Cl.
*A61B 1/012* (2006.01)
*A61B 1/273* (2006.01)
*A61B 18/12* (2006.01)
*A61B 18/00* (2006.01)

(52) U.S. Cl.
CPC .......... *A61B 2018/1475* (2013.01); *A61B 2018/1495* (2013.01)

(56) References Cited

U.S. PATENT DOCUMENTS

| | | | | |
|---|---|---|---|---|
| 5,327,889 | A * | 7/1994 | Imran | A61B 5/0422 600/373 |
| 5,468,928 | A * | 11/1995 | Yelvington | A61M 5/3278 219/68 |
| 5,487,385 | A * | 1/1996 | Avitall | A61B 5/0422 600/374 |
| 5,662,647 | A * | 9/1997 | Crow | A61B 18/14 606/41 |
| 5,824,030 | A * | 10/1998 | Yang | A61N 1/056 600/374 |
| 6,086,583 | A | 7/2000 | Ouchi | |
| 6,178,354 | B1 * | 1/2001 | Gibson | A61B 18/1492 607/116 |
| 6,451,016 | B1 | 9/2002 | Karakozian | |
| 6,464,698 | B1 * | 10/2002 | Falwell | A61B 18/1492 606/41 |
| 6,544,226 | B1 * | 4/2003 | Gaiser | A61B 1/00089 604/106 |
| 7,052,491 | B2 * | 5/2006 | Erb | A61B 18/14 606/14 |
| 7,169,115 | B2 | 1/2007 | Nobis et al. | |
| 7,507,238 | B2 | 3/2009 | Edwards et al. | |
| 2002/0065515 | A1 * | 5/2002 | Falwell | A61B 18/1492 606/41 |
| 2002/0193851 | A1 * | 12/2002 | Silverman et al. | 607/101 |
| 2003/0130565 | A1 * | 7/2003 | Muller | A61B 1/00071 600/156 |
| 2003/0167056 | A1 | 9/2003 | Jahns et al. | |
| 2003/0181900 | A1 | 9/2003 | Long | |
| 2003/0181905 | A1 * | 9/2003 | Long | A61B 18/1492 606/46 |
| 2004/0193152 | A1 * | 9/2004 | Sutton | A61B 18/1477 606/48 |
| 2005/0203488 | A1 | 9/2005 | Michlitsch et al. | |
| 2006/0259027 | A1 * | 11/2006 | Kwan | A61B 18/1477 606/41 |
| 2008/0262301 | A1 | 10/2008 | Gibbons et al. | |
| 2009/0012518 | A1 * | 1/2009 | Utley | A61B 18/1492 606/41 |
| 2009/0093675 | A1 | 4/2009 | Surti | |
| 2010/0298761 | A1 * | 11/2010 | Staal | A61N 1/327 604/20 |
| 2012/0226271 | A1 * | 9/2012 | Callas | A61B 18/148 606/33 |
| 2016/0331450 | A1 * | 11/2016 | Ben-Ezra | A61B 18/1492 |

OTHER PUBLICATIONS

Written Opinion dated Nov. 17, 2011 for International Application No. PCT/US2011/047708.

* cited by examiner

ABLATION OVERTUBE

RELATED APPLICATIONS

This application claims the benefit of U.S. Provisional Application No. 61/378,732, filed Aug. 31, 2010, which is incorporated by reference herein in its entirety.

BACKGROUND

Millions of people suffer from progressive gastroesophageal reflux disease (GERD) which is characterized by frequent episodes of heartburn, typically on at least a daily basis. Without adequate treatment, GERD can cause erosion of the esophageal lining as the lower esophageal sphincter (LES), a segment of smooth muscle located at the junction of the stomach and the esophagus, gradually loses its ability to function as the barrier that prevents stomach acid reflux. Chronic GERD can also cause metaplasia to the inner lining of the esophagus where the normal squamous mucosa changes to columnar mucosa, also known as Barrett's esophagus. Barrett's esophagus can progress to esophageal cancer if left untreated.

Endoscopic treatment of Barrett's esophagus includes endoscopic mucosal resection (EMR). One method of performing EMR involves ablation of the mucosal surface by heating the surface until the surface layer is no longer viable. The dead tissue is then removed.

Treatment devices for performing EMR have been developed using bipolar ablation technology that includes circumferentially oriented electrodes to endoscopically ablate the diseased tissue. Typically, the circumferentially oriented electrodes are positioned on an inflatable balloon. The balloon must be inflated to a predetermined size to achieve adequate contact with the diseased tissue for delivery of the appropriate amount of energy from the bipolar ablation device to ablate the diseased tissue. In order to determine the correct size and balloon pressure to achieve adequate ablation, a sizing balloon must first be introduced into the esophagus. Once the proper measurements are made with the sizing balloon, the treatment device can then be endoscopically inserted into the patient's esophagus. The balloon inflated treatment device and procedure requires an additional step to size the balloon and adds more time and potential patient discomfort to the treatment procedure. In addition, the inflated balloon is positioned in front of the endoscope viewing window, preventing direct visualization of the target tissue and potentially leading to ablation of healthy tissue or incomplete ablation of diseased tissue.

What is needed in the art is an ablation treatment device that is simple to use, that minimizes the number of steps in a treatment procedure and that provides treatment under direct endoscopic visualization.

BRIEF SUMMARY

Accordingly, it is an object of the present invention to provide a device and a method having features that resolve or improve on one or more of the above-described drawbacks.

In one aspect of the present invention, an energy delivery system is provided. The energy delivery system includes an overtube. The overtube includes a body having a proximal portion, a distal portion and a lumen extending at least partially therethrough. The proximal portion is adapted to be positioned over a distal portion of an endoscope. The body also includes a plurality of openings formed in the body and connected to the lumen and an electrode operably connected to the body and extending over at least a portion of a surface of the body. The lumen is operably connectable to a vacuum source and the electrode is operably connectable to a power source.

In another aspect of the present invention, a method of delivering energy to a tissue site within a patient's lumen is provided. The method includes positioning an energy delivery system within a patient's lumen. The energy delivery system includes an overtube having a body including a proximal portion, a distal portion and a lumen extending at least partially therethrough. The overtube also includes a plurality of openings formed in the body and connected to the lumen; and an electrode operably connected to the body and extending over at least a portion of a surface of the body. The method further includes applying suction to the plurality of openings, drawing the tissue site to be treated to the body using suction and applying energy to the tissue site.

DETAILED DESCRIPTION

Figure 1:
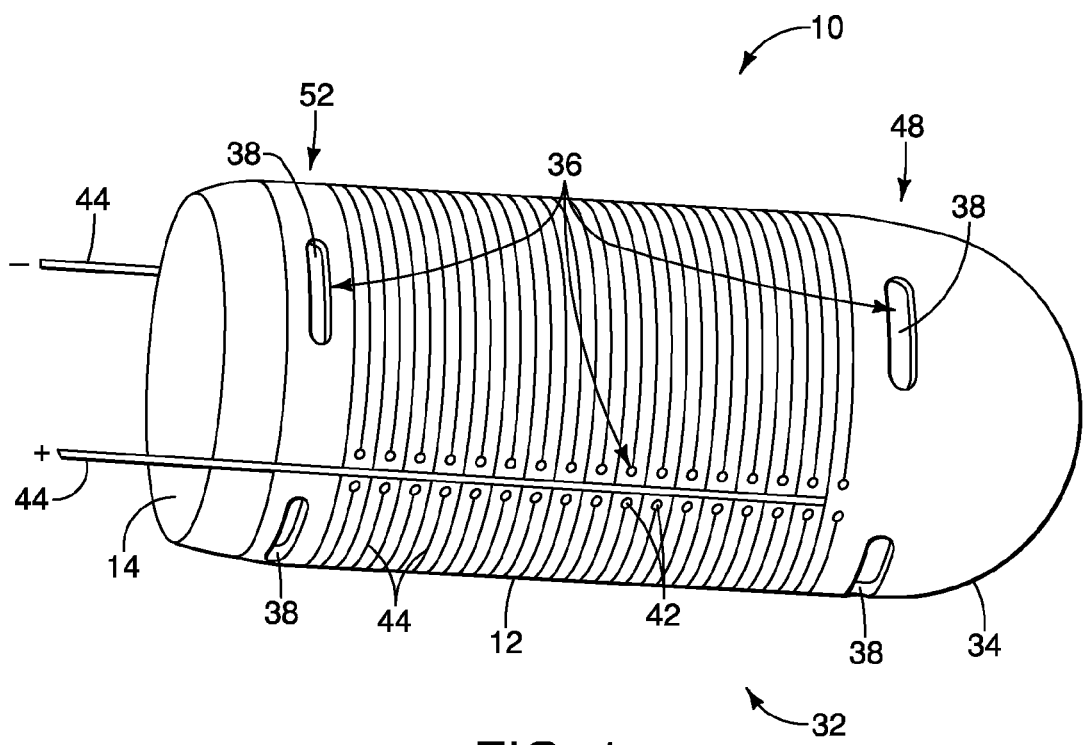
FIG. 1 is a side view of an ablation overtube in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the ablation overtube that is farthest from the physician and the term "proximal" means the portion of the ablation overtube that is nearest to the physician.

Figure 2A:
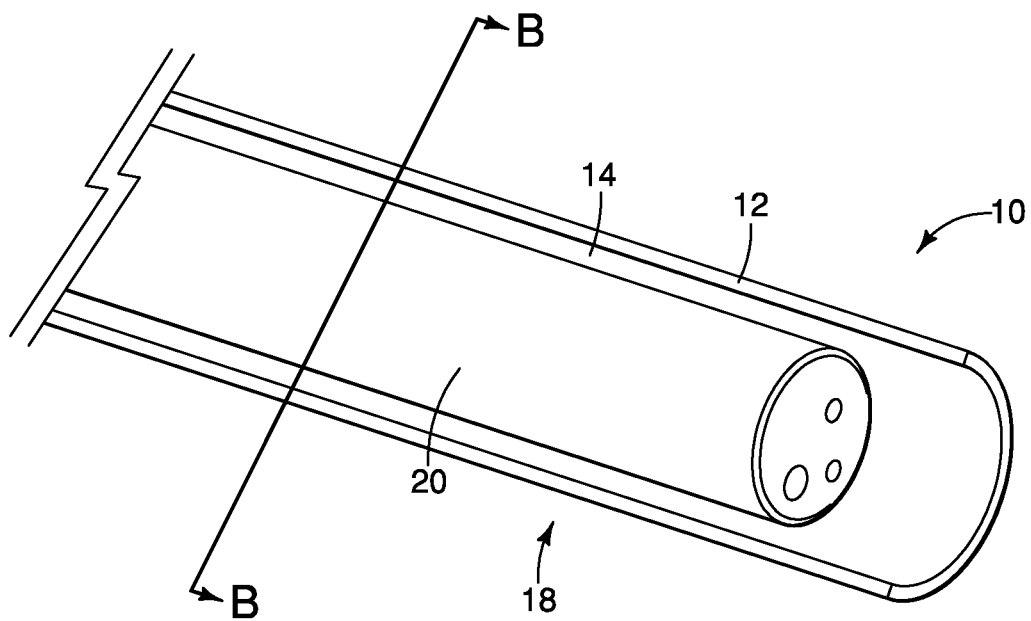
FIG. 2A is partial sectional view of the ablation overtube shown in FIG. 1 positioned over an endoscope.
Figure 2B:
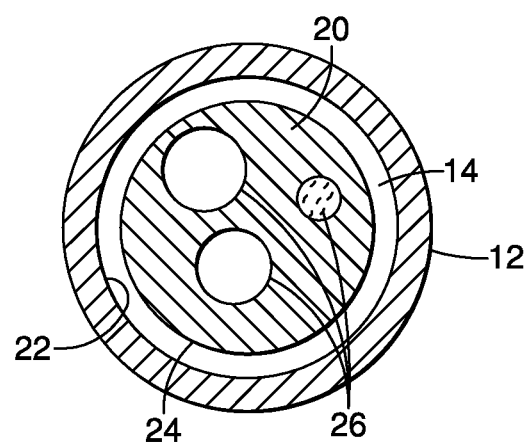
FIG. 2B is a cross-sectional view across B-B shown in FIG. 2A.

FIG. 1 illustrates an embodiment of an ablation overtube 10 in accordance with the present invention. As shown in FIG. 2A, the ablation overtube 10 includes a tubular body 12 having a lumen 14 formed therein. The lumen 14 of the body 12 is sized to fit over a distal end 18 of a conventional endoscope 20. A cross sectional view of the endoscope 20 and the overtube 10 is shown in FIG. 2B. The overtube 10 has a length suitable for accessing the desired target tissue, but is generally shorter than the working length of the endoscope 20. As shown in FIG. 2B, the endoscope 20 includes a plurality of lumens 26 formed therein that may be used as a working channel, a viewing port for a viewing device, a flush port, a wire guide port and the like.

A distal end portion 32 of the overtube 10 is shown in FIG. 1 and includes a curvilinear distal end 34. The distal end 34 is shaped for non-traumatic delivery through the patient's lumen and may be domed, conical, oval and the like. A plurality of openings 36 are also provided on the distal end portion 32. The openings 36 are used for suctioning the tissue into proximity to the ablation overtube 10. The openings 36 may also be used for fluid delivery or additional separate openings may be provided to deliver fluid to the tissue during ablation. The plurality of openings 36 may include at least one first opening 38 and at least one second opening 42. As shown in FIG. 1, the first openings 38 are larger than second openings 42. In some embodiments, the openings 36 may all be similarly sized or the first openings 38 may be smaller than the second openings 42. A first plurality 48 of first openings 38 may be positioned circumferentially around the distal portion 32 of the overtube 10. By way of non-limiting example, the first plurality 48 of first openings 38 may include openings 38 that are positioned on the body 12 and spaced apart by 180°, 90°, or any other suitable spacing. Other positions for the first plurality 48 of the openings 38 may also be used and may be asymmetrically or symmetrically positioned around the overtube 10. Two, three or more first openings 38 may be included in the first plurality 48.

A second plurality 52 of first openings 38 may also be included on the distal portion 32 of the overtube 10 and positioned proximal to the first plurality 48 of first openings 38. The positioning of the second plurality 52 of first openings 38 may be the same as the first plurality 48, or may be different in number, in spacing or in both. As shown in FIG. 1, and by way of non-limiting example, the second openings 42 extend longitudinally in a row 54 on the distal portion 32 of the overtube 10. A plurality of longitudinal rows 54 of second openings 42 may be positioned circumferentially around the distal portion 32. As shown in FIG. 1, a pair of rows 54 of second openings 42 may be provided next to each other. In some embodiments, the rows 54 may be spaced apart by 180°, 90°, or any other suitable spacing. The second openings 42 may also extend in rows spiraling around the distal portion 42, in a zig zag pattern or in other patterns on the distal portion 32 of the overtube 10. Openings 36 on different portions of the ablation overtube 10 may be activated independently depending on how much tissue is to drawn to the overtube 10 and ablated.

The distal portion 32 of the ablation overtube 10 also includes at least one electrode 44 or a plurality of electrodes 44 as shown in FIG. 1. The electrodes 44 are shown as a plurality of circumferentially extending bands 46 substantially encircling the distal portion 32 of the ablation overtube 10. In some embodiments, the electrodes 44 may extend about 3 mm to about 90 mm longitudinally along the distal portion 32 of the overtube 10. As shown in FIG. 1, the electrodes 44 extend between the first and second plurality 48, 52 of first openings 38. The pattern of the electrodes 44 may include substantially circumferential bands having a plurality of bands adjacent to each other, a plurality of longitudinally extending strips, extending between the proximal openings 52 and the distal openings 48, angled or helical patterns, circular patterns or any other pattern suitable for ablation of the target tissue. By way of non-limiting example, if the electrodes 44 cover an area about 360° around an ablation overtube, a section of 180° may be independently activated from the remaining 180° electrode section. Alternatively, electrodes may be provided to cover, 45°, 90°, 180° or other section sizes on the ablation overtube 10.

Figure 3:
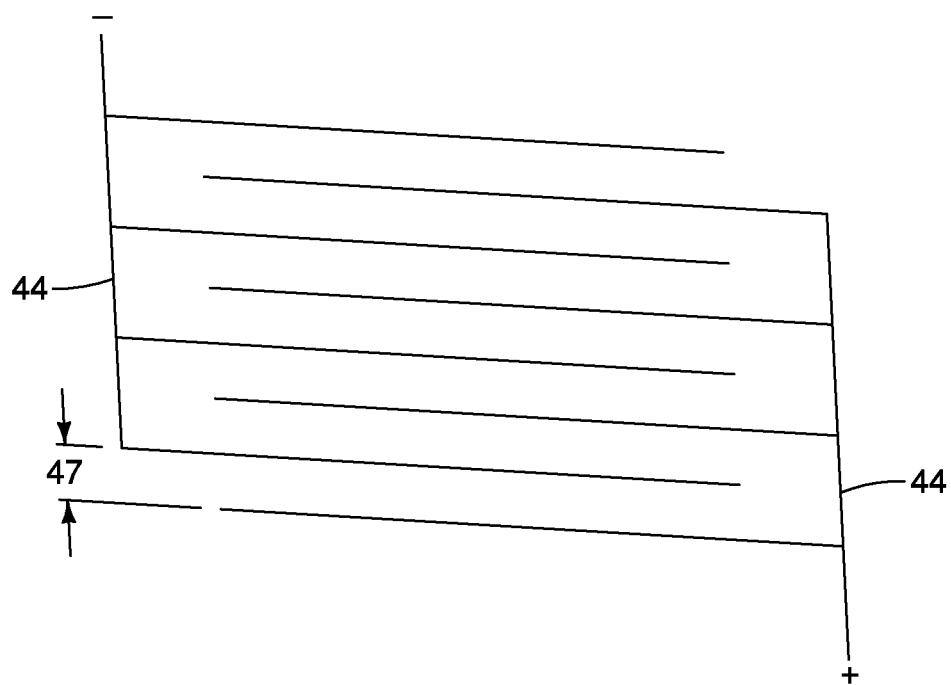
FIG. 3 is a partial view of electrodes in accordance with an embodiment of the present invention.

As shown in FIGS. 1 and 3, the electrodes 44 may be provided in pairs to form a bipolar delivery device. One electrode 44 of the pair is a positive electrode and other electrode 44 of the pair is a negative electrode. The positive and negative electrodes 44 alternate in the pattern as shown in FIG. 3. Distance 47 between the electrodes 44 may be optimized to control the depth of ablation of the target tissue. The distance 47 between positive and negative electrodes 44 may be between about 0.05 mm and about 5 mm, but is not limited to these distances. In some embodiments, the electrodes 44 may cover a portion of the ablation overtube 10 or be selectively energizable so that only a portion of the ablation overtube contacting the tissue to be treated is activated. By way of non-limiting example, the electrodes 44 may be selectively energizable in a portion extending 360° around the overtube 10 and may extend for a length of about 1-100 mm although greater lengths may also be used. Non-limiting examples of selective activation could include an energizable portion extending 360° around the overtube 10 and extending longitudinally about 6 cm, or in a portion extending 360° and extending longitudinally about 1 cm, 10 cm, 20 cm, etc. or in a portion extending about 90° and extending longitudinally about 1, 2, 10, 20 or 50 cm. Other activation configurations for selectively energizing portions of the electrodes are also possible and depend on the target tissue, the depth of the lesion, the type of energy, the length of application of the energy to the tissue and the like.

In some embodiments, one or more electrodes 44 may be provided as a monopolar delivery device and may include a grounding pad or an impedance circuit (not shown). As shown in FIG. 1, the second openings 42 are co-extensive with the electrodes 44 so that the tissue may be suctioned onto the electrodes for ablation. The electrodes 44 connect to a power source 310 shown in FIG. 6 to supply energy to the electrodes 44 to ablate the tissue when suction is applied to the openings 36 to pull the tissue to the ablation overtube 10. The power source may be any suitable source for delivering power for a surgical procedure. The power source 310 may be a radio frequency source. However, other types of power sources may also be used to provide energy to the electrodes 44. By way of non-limiting example, additional possible energy sources may include microwave, ultraviolet and laser energies.

Figure 4A:
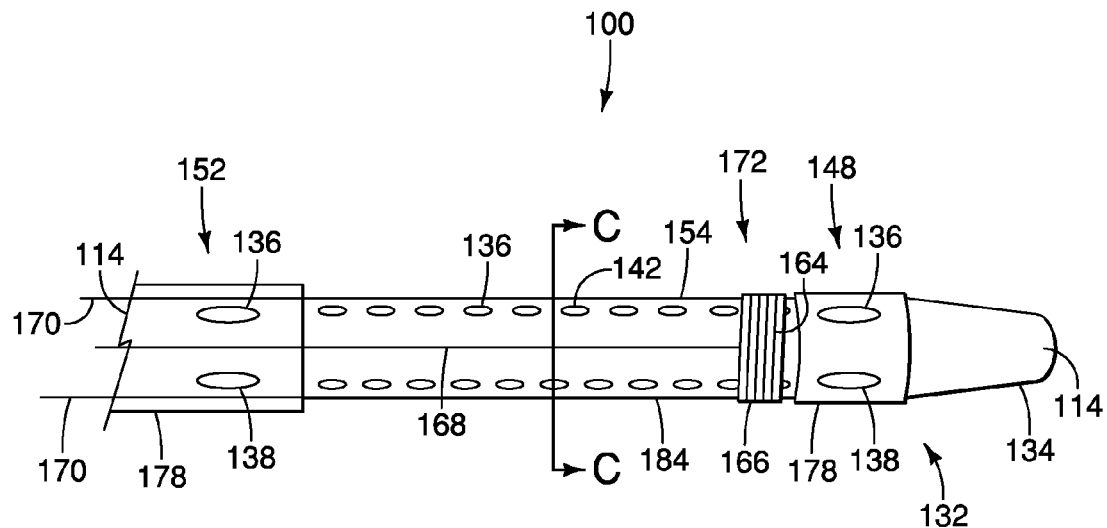
FIG. 4A is a side view of an embodiment of an ablation overtube with a moveable member in a first position.
Figure 4B:
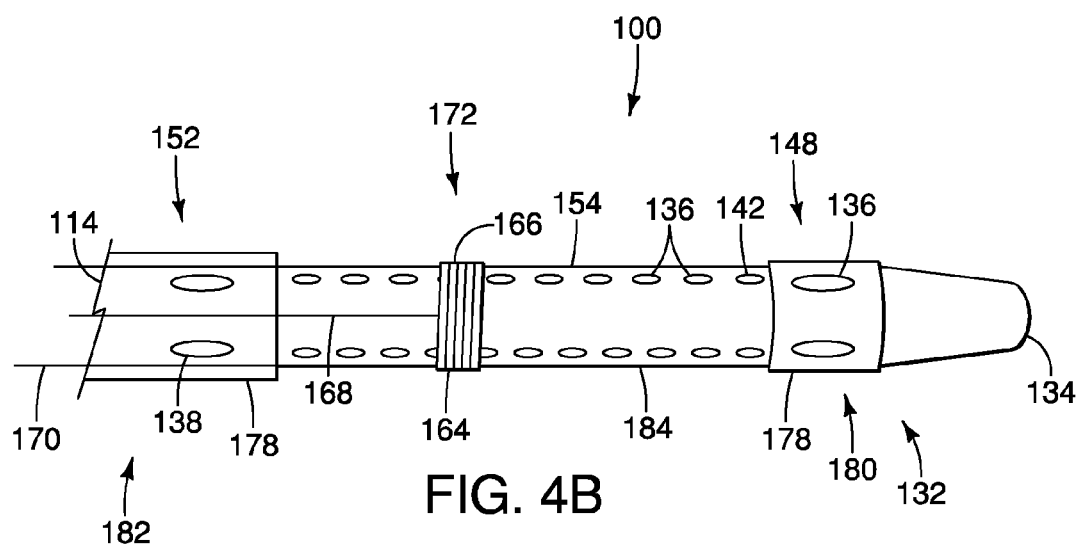
FIG. 4B is a side view of the embodiment of the ablation overtube shown in FIG. 4A with a moveable member in a second position.

FIGS. 4A and 4B illustrate an alternative embodiment of an ablation overtube 100 in accordance with the present invention. The ablation overtube 100 includes a tubular body 112 having a lumen 114 formed therein. Similar to the ablation overtube 10 described above, the lumen 114 of the body 112 is sized to fit over a distal end 18 of a conventional endoscope 20. A distal end portion 132 of the overtube 100 is shown in FIGS. 4A and 4B and includes a curvilinear distal end 134. The distal end 134 is shaped for non-traumatic delivery through the patient's lumen and may be domed, conical, oval and the like. A plurality of openings 136 are also provided on the distal end portion 132. The openings 136 are used for suctioning the tissue into proximity to the ablation overtube 100. The openings 136 may also be used for fluid delivery or additional separate openings may be provided to deliver fluid to the tissue during ablation. The plurality of openings 136 may include at least one first opening 138 and at least one second opening 142. As shown in FIG. 4A, the first openings 138 are larger than second openings 142. In some embodiments, the openings 136 may all be similarly sized or the first openings 138 may be smaller than the second openings 142. A first plurality 148 of first openings 138 may be positioned circumferentially around the distal portion 132 of the overtube 100. By way of non-limiting example, the first plurality 148 of first openings 138 may include openings 138 that are positioned on the body 112 and spaced apart by 180°, 90°, or any other suitable spacing. Other positions for the first plurality 148 of the openings 138 may also be used and may be asymmetrically or symmetrically placed. Two, three or more first openings 138 may be included in the first plurality 148.

A second plurality 152 of first openings 138 may also be included on the distal portion 132 of the overtube 100 and positioned proximal to the first plurality 148 of first openings 138. The positioning of the second plurality 152 of first openings 138 may be the same as the first plurality 148, or may be different in number, in spacing or in both. As shown in FIGS. 4A and 4B, and by way of non-limiting example, the second openings 142 extend longitudinally in a row 154 on the distal portion 132 of the overtube 100. A plurality of longitudinal rows 154 of second openings 142 may be positioned circumferentially around the distal portion 132, by way of non-limiting example the rows 154 may be spaced apart by 180°, 90°, or any other suitable spacing. The second openings 142 may also extend in rows spiraling around the distal portion 132, in a zig zag pattern or in other patterns on the distal portion 132 of the overtube 100.

Figure 6:
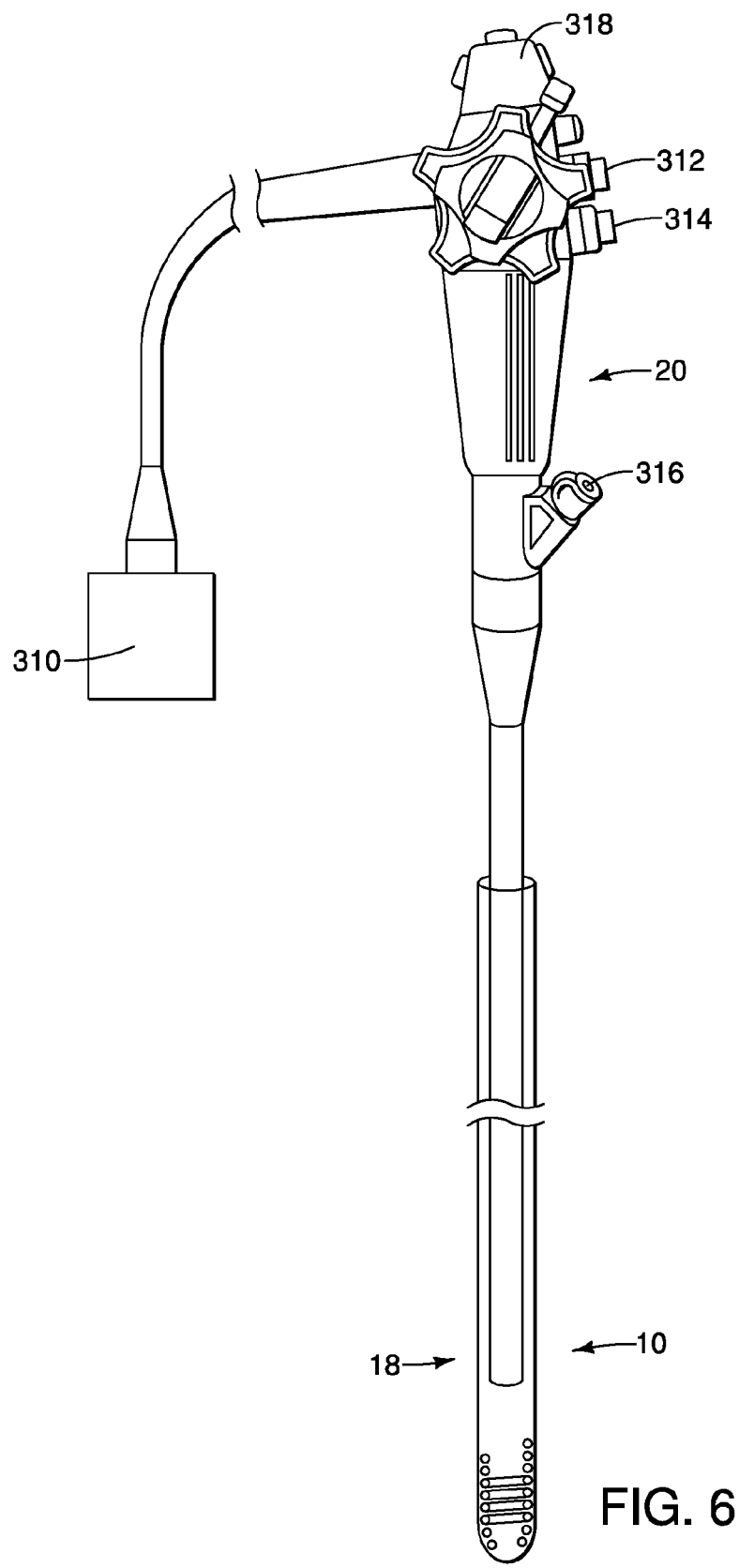
FIG. 6 is a view of an embodiment of an ablation overtube and an endoscope.

The distal portion 132 of the ablation overtube 100 also includes at least one electrode 164 or a plurality of electrodes 164. The electrodes 164 may be provided in pairs for a bipolar device or individually for a monopolar device as described above with reference to electrodes 44. As shown in FIGS. 4A and 4B, the electrodes 164 are positioned on a movable member 166. The movable member 166 is slidably positionable on the distal portion 132 of the overtube 100. The moveable member 166 may be moved proximally and distally along the distal portion 132 to move the electrodes 164 proximally and distally. The ablation overtube 100 may further include one or more drive cables 168 connecting to the movable member 166 and extending proximally so that the operator can control the movement of the movable member 166. One or more guiding wires 170 may also be provided and connected to the movable member 166. The guiding wires 170 extend proximally to facilitate control of the movement of the movable member 166 by the operator so that the movable member 166 does not rotate if undesired. The drive cables 168 and/or the guide wires 170 may be connected to a power source 310 connected to the endoscope 20 as shown in FIG. 6 to supply energy to the electrodes 164 to ablate the tissue. The electrodes 164 are shown as a plurality of circumferential bands substantially encircling the movable member 166. Similar to the electrodes 44 described above, the pattern of the electrodes 164 may be any pattern suitable for ablation and the bands are shown by way of non-limiting example. In some embodiments, the electrodes 164 may extend about 3 mm to about 30 mm longitudinally along the movable member 166, but are not limited to these distances. Similar to the electrodes 44 described above, the electrodes 164 may be selectively activatable so that a portion of the electrodes 164 are activated and a portion of the electrodes 164 are not energized. As shown in FIG. 4A, the moveable member 166 and the electrodes 164 are at a first position 172 on the distal portion 132 of the overtube 100. FIG. 4B illustrates the movable member 166 and the electrodes 164 at a second position 174 on the distal portion 132 of the overtube 100 that is proximal to the first position 172. The moveable member 166 and the electrodes 164 may be positioned anywhere along the distal portion 132 of the ablation overtube 100 to allow the physician to deliver a precise ablation energy to the target tissue and to reposition the electrodes 164 at another site directly adjacent to or close to the first site as described in more detail below. In some embodiments, the moveable member 166 extends between the first and second plurality 148, 152 of first openings 138. The second openings 142 may be positioned along the path of the moveable member 166 so that the tissue may be suctioned to the distal portion 132 of the body 112 and onto the electrodes 164 at any position of the movable member 166. As shown in FIGS. 4A and 4B, the movable member does not extend beyond the distal end 134.

The overtube 100 may further include one or more sheaths 178 that are positioned over the body 112 and sized and shaped to receive the movable member 166 therein. As shown in FIG. 4B, the sheath 178 may be positioned at a distal position 180 and/or at a proximal position 182 so that the movable member 166 and the electrodes 164 may be slidably positioned between the sheath 178 and the body 112 of the overtube 110. The sheath 178 may be sized to receive the drive cables 168 and the guiding wires 170 therein. The sheath 178 may also be sized to closely fit over the moveable member 166 to remove any tissue remnants that adhere to the movable member 166 after ablation of the tissue by slidably moving the movable member 166 into the sheath 178.

Figure 4C:
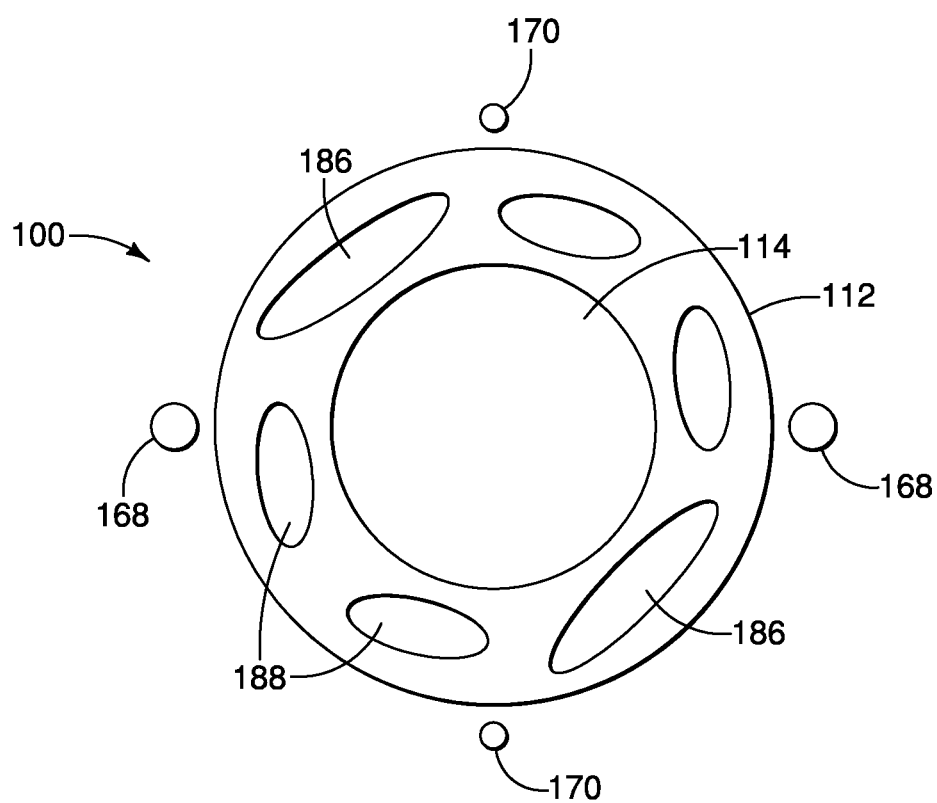
FIG. 4C is a cross-sectional view across C-C shown in FIG. 4A.

Flush ports 184 may also be provided in the body 112 for flushing the tissue and the electrodes 164. The flush ports 184 may be alternated with the openings 136 provided for suctioning the tissue to the ablation overtube 100. In some embodiments, the body 112 may be provided with separate lumens connecting to the flush ports 184 and the openings 136. A cross-sectional view of the overtube 100 is shown in FIG. 4C. The body 112 includes the lumen 114 that receives the endoscope 20 (similar to the arrangement shown in FIG. 2A). In some embodiments, the lumen 114 may extend to the distal end 134 so that a wire guide (not shown) may extend therethrough to facilitate placement of the ablation overtube 100. One or more flushing lumens 186 are provided for connection to the flush ports 184 and a fluid source. One or more suction lumens 188 are provided for connection to the openings 136 and a suction source connectable to the endoscope 20 at the port 312 (see FIG. 6). The drive cables 168 and guiding wires 170 are also shown.

Figure 5A:
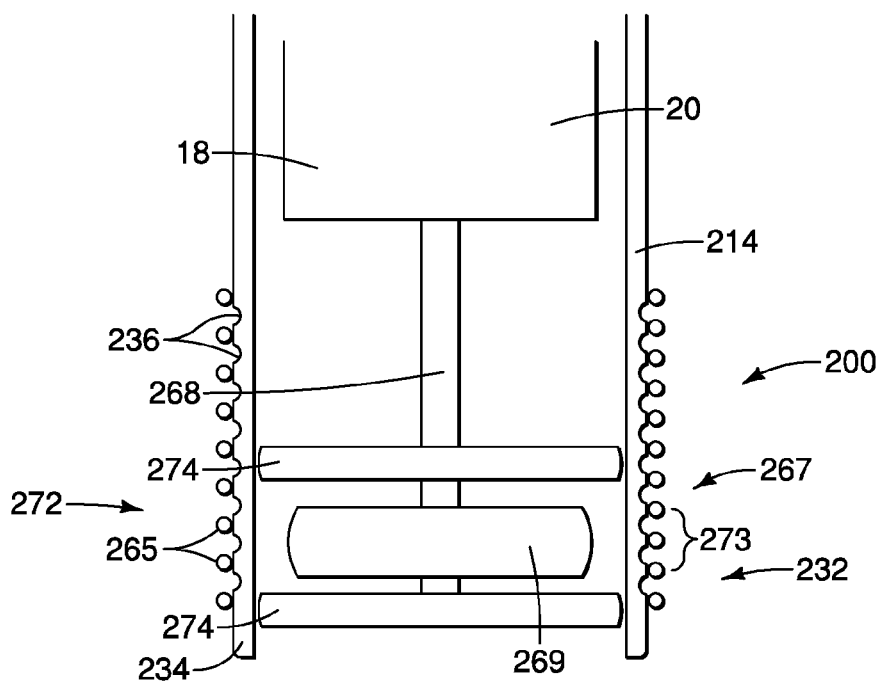
FIG. 5A is a sectional view of an alternative embodiment of an ablation overtube in accordance with the present invention.
Figure 5B:
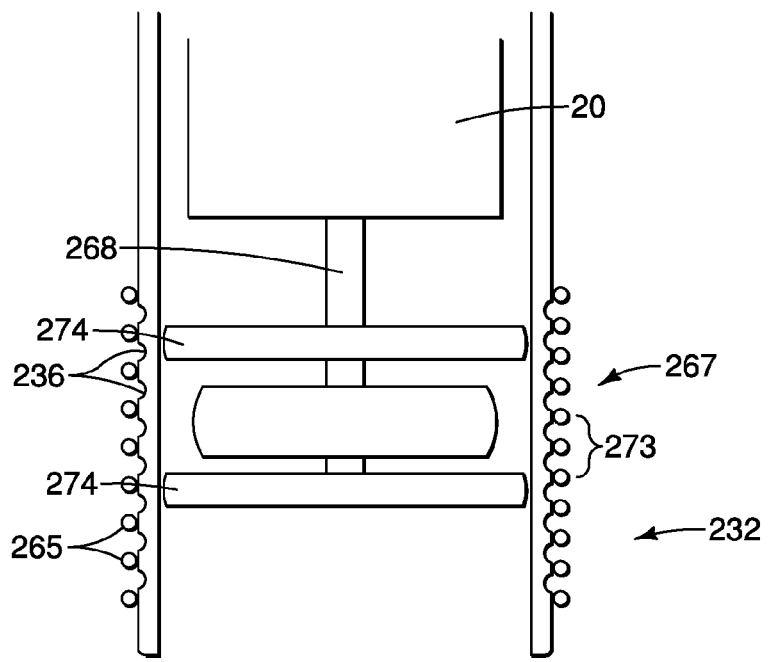
FIG. 5B is a sectional view of the embodiment shown in FIG. 5A.

FIGS. 5A and 5B illustrate an alternative embodiment of an ablation overtube 200 in accordance with the present invention. The ablation overtube 200 includes a tubular body 212 having a lumen 214 formed therein. Similar to the ablation overtube 10 described above, the lumen 214 of the body 212 is sized to fit over a distal end 18 of a conventional endoscope 20. A distal end portion 232 of the overtube 200 is shown in FIGS. 5A and 5B. The distal end 234 may be open as shown, or closed and/or curvilinear. A plurality of openings 236 may be provided on the distal end portion 232. Similar to the openings 36 described above, the openings 236 are used for suctioning the tissue into proximity to the ablation overtube 200. The openings 236 may also be used for fluid delivery or additional separate openings may be provided to deliver fluid to the tissue during ablation. The openings 236 may be provided in different sizes and different patterns as described above. The distal portion 232 of the ablation overtube 200 also includes at least one electrode 265 or a plurality of electrodes 265. As shown in FIGS. 5A and 5B, the electrodes 265 are positioned on the distal portion 232 of the body 212. The electrodes 265 may be provided in any suitable pattern on the body 212, including a plurality of rings, spirals or geometric patterns. Similar to the electrodes 44 described above, the electrodes 265 may be selectively activatable so that a portion of the electrodes 265 are activated and a portion of the electrodes 265 are not energized.

The ablation overtube 200 may also include a movable member 267 that is slidably positionable within the lumen 214 of the body 212 of the overtube 200. The moveable member 267 may be moved proximally and distally within the lumen 214. The movable member 267 may be provided with an energy source 269 to transfer energy to the electrodes 265 for tissue ablation. For example, the energy source 269 may be a magnet that is activatable by the physician. The magnet can be rotated about a fixed axis to induce a current to transfer energy to the electrodes 265. By way of another non-limiting example, the energy source 269 may be activatable to provide thermal energy that is transferable to the electrodes 265 for tissue ablation. Shielding members 274 may be provided to shield the energy source 269 and to limit the dissipation of energy from the energy source 269 to only the targeted tissue. The energy source 269 and the shielding 274 may be connected to one or more drive cables 268 that may extend through the lumen 214 of the overtube 200 and through the endoscope 20 so the user can control the movement of the energy source 269 proximally and distally and to provide connection to a power source 310.

As shown in FIG. 5A, the moveable member 267 is shown at a first position 272 within the distal portion 232 of the overtube 200. The electrodes 265 that are activatable by the energy source 269 with the moveable member 267 in the first position 272 are indicated by a first region 273 on the body 212. FIG. 5B illustrates the movable member 267 and the electrodes 164 at a second position 174 on the distal portion 132 of the overtube 100 that is proximal to the first position 172. The moveable member 166 and the electrodes 164 may be positioned anywhere along the distal portion 132 of the ablation overtube 100 to allow the physician to deliver a precise ablation energy to the target tissue and to reposition the electrodes 164 at another site directly adjacent to or close to the first site as described in more detail below. In some embodiments, the moveable member 166 extends between the first and second plurality 148, 152 of first openings 138. The second openings 142 may be positioned along the path of the moveable member 166 so that the tissue may be suctioned to the distal portion 132 of the body 112 and onto the electrodes 164 at any position of the movable member 166.

The endoscope 20 is shown in FIG. 6 with the ablation overtube 10 positioned over the distal end 18 of the endoscope 20. The overtube 10 is shown by way of non-limiting example and the other embodiments of the ablation overtube may also be similarly positioned over the distal end 18 of the endoscope 20. The endoscope 20 may include a suction port 312 for connecting to a suction source to provide the suction to pull the tissue to the ablation overtube 10. The endoscope 20 may also include a flush port 314, a working channel 316 and a video control portion 318.

In some embodiments, the ablation overtube is made primarily of a substantially transparent or translucent polymer such as polytetrafluorothylene (PTFE). Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon. In some embodiments, the ablation overtube or a distal portion of the ablation overtube is formed from a lubricious material such as PTFE and the like for easy slidability within the patient's lumen for delivery to the treatment site. The ablation overtube or a portion thereof may also be coated or impregnated with other compounds and materials to achieve the desired properties. Exemplary coatings or additives include, but are not limited to, parylene, glass fillers, silicone hydrogel polymers and hydrophilic coatings.

The electrodes may be secured to the body of the ablation overtube by any method know to one skilled in the art, By way of non-limiting example, the electrodes may be secured by gluing, bonding, taping, an adhesive backing on the electrodes, crimping, manufacturing the electrodes directly on to the body and the like.

Figure 7B:
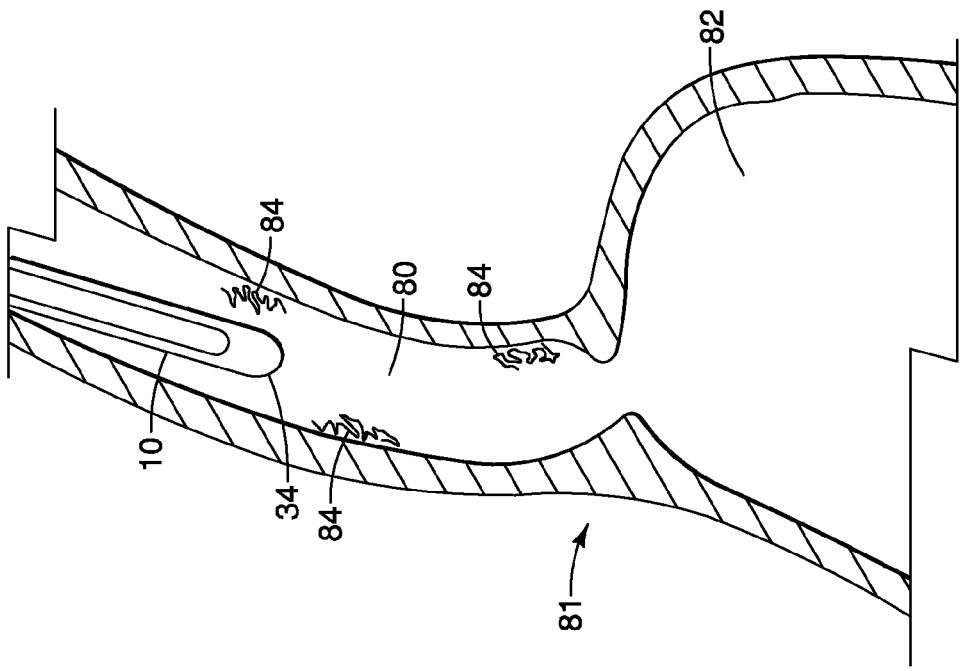
FIGS. 7A, 7B and 7C illustrate operation of the ablation overtube.
Figure 7A:
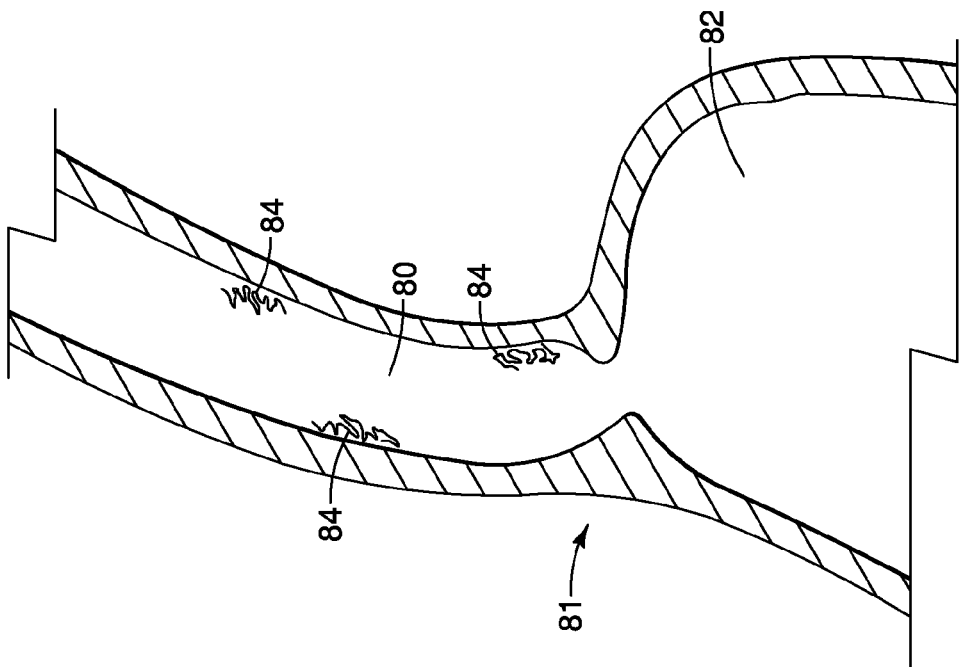
Figure 7C:
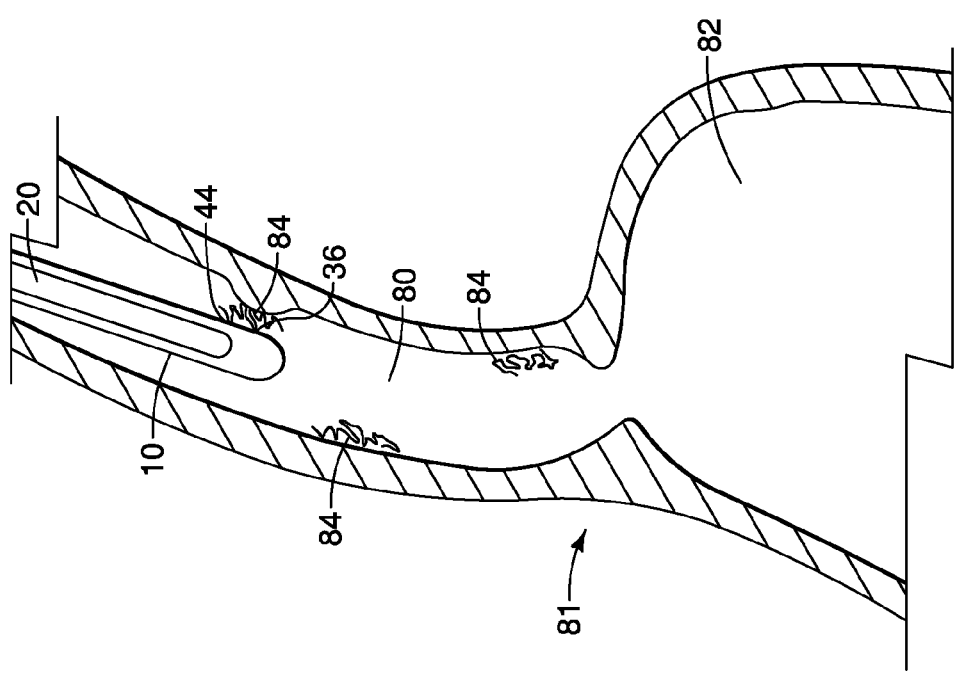

Operation of the ablation device using the ablation overtube 10 as an example will be explained with reference to FIGS. 7A-7C. FIG. 7A illustrates a patient's esophagus 80, lower esophageal sphincter (LES) 81 and stomach 82. Areas of diseased tissue 84 within the esophagus 80 are also shown. The diseased tissue 84 may be columnar mucosa (Barrett's esophagus) that is to be ablated using the ablation overtube 10. FIG. 7B illustrates the distal portion 34 of the ablation overtube 10 positioned over the endoscope 20 and the overtube 10 and the endoscope 20 being inserted into the patient's esophagus 80. The ablation overtube 10 is positioned in the esophagus 80 near the portion of the diseased tissue 84 to be treated. The insertion of the ablation overtube 10 may be monitored using the viewing port of the endoscope to help position the overtube 10 at the diseased tissue. As shown in FIG. 7C, the diseased tissue 84 has been pulled to the ablation overtube 10 using the vacuum pulled through one or more of the openings 36 in the ablation overtube 10. The diseased tissue has been brought into contact with the electrodes 44 or an electroconductive fluid flushed through one or more of the openings 36. The power source 310 is activated for a sufficient time to ablate the diseased tissue 84. The vacuum is released and the ablation overtube is moved away from the tissue 84. The overtube 10 may be rinsed through the openings 36 to move any adherent tissue. The ablation overtube 10 may be repositioned near another portion of diseased tissue 84 for treatment and the steps repeated as many times as needed. While the procedure has been described with reference to the ablation of diseased tissue in the esophagus using the ablation overtube 10, the location of the treatment is not limited to the esophagus. By way of non-limiting example, portions of the stomach, or the gastrointestinal tract may also be treated using the ablation overtube 10.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An energy delivery system comprising:
   an overtube comprising:
   a body having a proximal portion and a distal portion, the proximal portion is adapted to be positioned over a distal portion of an endoscope, the body further comprising a lumen extending at least partially therethrough;
   a first plurality of openings formed in the body, extending from an outer surface of the body and connected to the lumen, the lumen being operably connectable to a vacuum source; and
   an electrode operably connected to the body and disposed over at least a portion of the outer surface of the body; wherein the electrode is mounted on a movable member, the movable member extending entirely around a circumference of the outer surface of the body and free from contact with the lumen of the body, the electrode extending circumferentially around the moveable member, the movable member is longitudinally movable along the outer surface and selectively positionable at a first position on the outer surface of the body and at a second position on the outer surface of the body, the second position being proximal to the first position on the outer surface of the body; and the electrode being operably connectable to a power source and being energizable at the first position and the second position.

2. The energy delivery system of claim 1, wherein the first plurality of openings extend longitudinally along a portion the body.

3. The energy delivery system of claim 2, wherein the first plurality of openings comprise at least two rows of openings extending longitudinally along a portion of the body.

4. The energy delivery system of claim 2, further comprising a second plurality of openings extending circumferentially around a portion of the body.

5. The energy delivery system of claim 4, wherein the second plurality of openings are larger than the first plurality of openings.

6. The energy delivery system of claim 1, wherein a portion of the electrodes are selectively activatable.

7. The energy delivery system of claim 1, wherein the system further comprises a drive cable to movably position the electrode.

8. The energy delivery system of claim 7, further comprising a sheath to receive at least a portion of the movable electrode therein.

9. The energy delivery system of claim 1, wherein the body comprises a transparent material or a translucent material.

10. The energy delivery system of claim 1, further comprising an endoscope, the body being positionable over the endoscope.

11. The energy delivery system of claim 1, wherein the electrode is at least partially circumferentially positioned over an outer surface of the movable member.

12. The energy delivery system of claim 1, further comprising a first sheath and a second sheath, the second sheath positioned distal to the first sheath so that a portion of the body is unsheathed between the first and second sheaths.

13. An energy delivery system comprising:
    an overtube comprising:
    a body having a proximal portion and a distal portion and a lumen extending at least partially therethrough, the proximal portion is adapted to be positioned over a distal portion of an endoscope;
    a first plurality of openings formed in the body, extending from an outer surface of the body and connected to the lumen, the lumen being operably connectable to a vacuum source; and
    an electrode operably connected to the body and disposed over at least a portion of the outer surface of the body; the electrode being operably connectable to a power source, the electrode extending entirely around a circumference of the outer surface of the body and being longitudinally movable along the outer surface and selectively positionable at a first position on the outer surface of the body and at a second position on the outer surface of the body, the second position being proximal to the first position on the outer surface of the body, the electrode being energizable at the first position and the second position.

14. The energy delivery system of claim 13, comprising a second plurality of openings formed in the body and connected to the lumen.

15. The energy delivery system of claim 13, wherein electrode is positioned on a movable member to selectively position the electrode at the first position and the second position.

16. The energy delivery device of claim 15, further comprising a sheath wherein the sheath is sized and shaped to remove tissue remnants from the movable member when the movable member is positioned at least partially within the sheath.

17. An energy delivery system comprising:
    an overtube comprising:
    a body having a proximal portion and a distal portion, the proximal portion is adapted to be positioned over a distal portion of an endoscope, the body further comprising a lumen extending at least partially therethrough;
    a first plurality of openings formed in the body, extending from an outer surface of the body and connected to the lumen, the lumen being operably connectable to a vacuum source;
    a movable member extending entirely around the outer surface of the body;
    a drive cable to movably position the movable member, the drive cable positioned external to the lumen of the body; and
    an electrode mounted on the movable member and entirely surrounding a circumferences of the movable member, wherein the movable member is longitudinally movable along the outer surface and selectively positionable at a first position on the outer surface of the body and at a second position on the outer surface of the body, the second position being proximal to the first position on the outer surface of the body; and the electrode being operably connectable to a power source and being energizable at the first position and the second position.

\* \* \* \* \*